United States Patent [19]

Berger et al.

[11] Patent Number: 5,198,119
[45] Date of Patent: Mar. 30, 1993

[54] CONCENTRATION OR SEPARATION METHOD, COPOLYAMIDES AND COPOLYIMIDE AMIDES AND THE USE THEREOF

[75] Inventors: Joseph Berger, Basel, Switzerland; Wolfgang Wernet, Kobe, Japan

[73] Assignee: Ciba-Geigy Corporation, Ardsley, N.Y.

[21] Appl. No.: 744,622

[22] Filed: Aug. 12, 1991

[30] Foreign Application Priority Data

Aug. 17, 1990 [CH] Switzerland .............. 2675/90-6

[51] Int. Cl.$^5$ ............................................. B01D 61/00
[52] U.S. Cl. ............................... 210/654; 210/500.39
[58] Field of Search ............... 210/634, 644, 649–654, 210/500.37, 500.38, 500.39

[56] References Cited

U.S. PATENT DOCUMENTS

| | | | |
|---|---|---|---|
| 4,075,093 | 2/1978 | Walch et al. ............................ | 210/23 |
| 4,217,227 | 8/1980 | Elfert et al. ........................... | 210/500 |
| 4,694,061 | 9/1987 | Pfeifer . | |
| 4,714,669 | 12/1987 | Pfeifer et al. . | |
| 4,904,389 | 2/1990 | Waldhoff et al. ................... | 210/637 |

OTHER PUBLICATIONS

Chem. Abstract, vol. 13, No. 190 (C-593) (3538) May 8, 1989.
CA 110:25827c (1989).

Primary Examiner—Frank Sever
Attorney, Agent, or Firm—Kevin T. Mansfield; Edward McC. Roberts

[57] ABSTRACT

Mixtures of salts of organic carboxylic acids and organic compounds of non-salt character, dissolved in a $C_1$–$C_4$alkanol, can be concentrated or separated with a semipermeable membrane made from a copolyamide or copolyimide-amide which contains (a) a first aromatic diamine radical and (b) a second aromatic diamine radical which carries —$SO_3M$ groups, where M is $H^\oplus$, a monovalent to polyvalent metal cation or an ammonium cation. Provided the first diamine radical contains $C_1$–$C_4$alkyl groups in the o-positions to the amino groups, the copolymers are radiation-sensitive and can be used for producing protective layers or relief images, development being carried out in an aqueous alkaline medium.

17 Claims, No Drawings

CONCENTRATION OR SEPARATION METHOD, COPOLYAMIDES AND COPOLYIMIDE AMIDES AND THE USE THEREOF

The present invention relates to a process for concentrating or separating salts of organic carboxylic acids from organic compounds of non-salt character, which comprises contacting a solution of said salts and compounds in a low molecular alkanol with one side of a semipermeable membrane made from a copolyamide or copolyimide-amide which contains sulfonic acid groups, the pure low molecular alkanol being present on the other side of the membrane. The invention further relates to aromatic copolyamides and copolyimide-amides of two aromatic diamines, one of which contains sulfonic acid groups, and to a process for their preparation, as well as to a coated material and a process for the preparation of protective layers or relief images using said material.

Copolyamides of (1) diphenylsulfone diamines which are unsubstituted or alkyl-substituted in the nucleus, (2) aromatic diamines which contain sulfonic acid groups which may be in salt form, and aromatic dicarboxylic acids are, disclosed in Ca 110:25827c (1989). Semipermeable membranes made therefrom when used for the removal of salts from aqueous salt-containing solutions by reverse osmosis have an enhanced salt retention.

Surprisingly, it has been found that mixtures of salts of organic carboxylic acids and organic compounds of non-salt character, which mixtures are in the form of solutions in low molecular alkanols, can also be concentrated or separated with the aid of membranes made from copolyamides or copolyimide-amides in which one amine radical contains sulfonic acid groups which may be in salt form.

In one of its aspects, the invention relates to a process for concentrating or separating salts of organic carboxylic acids from organic compounds of non-salt character with the aid of semipermeable membranes, which process comprises contacting a solution of the salts and organic compounds in an unsubstituted or $C_1$-$C_3$alkoxy-substituted $C_1$-$C_4$alkanol, mixtures of such alkanols or mixtures of such alkanols with ethers, with one side of the membrane, the pure solvent being present on the other side of the membrane, and said membrane is made from a copolyamide or copolyimide-amide of (a) at least one aromatic dicarboxylic acid radical of 8 to 20 carbon atoms and/or (b) at least one trivalent aromatic tricarboxylic acid radical of 9 to 20 carbon atoms, each of which radicals is unsubstituted or substituted by halogen, nitro, $C_1$-$C_4$alkyl or $C_1$-$C_4$alkoxy, (c) at least one first divalent and/or trivalent mononuclear or binuclear aromatic diamine radical and (d) at least one second divalent and/or trivalent aromatic mononuclear or binuclear diamine radical containing at least one —$SO_3M$ group, each of which radicals is unsubstituted or substituted by halogen or $C_1$-$C_4$alkyl, and M is H$^\oplus$, a mono- to trivalent metal cation, $NH_4^\oplus$ or an organic ammonium cation of 1 to 30 carbon atoms.

The concentration of the salts and organic compounds is preferably 0.0001 to 10 percent by weight, more particularly 0.001 to 5 percent by weight and, most preferably, 0.001 to 3 percent by weight.

The thickness of the membrane may be from 5 to 300 μm, preferably from 20 to 200 μm.

M in the $SO_3M$ group as ammonium cation may be $NH_4^\oplus$ or an ammonium cation of a primary, secondary or tertiary open-chain amine containing preferably 1 to 24, most preferably 1 to 16, carbon atoms, or an ammonium cation of a monocyclic or bicyclic secondary or tertiary amine or of a tricyclic tertiary amine containing preferably 4 to 12 carbon atoms.

M as a metal cation can be a mono- to trivalent cation of metals of the main groups and subgroups, of the transition metals and of the noble metals. Mono- or divalent cations are preferred. Typical examples of metals are: Li, Na, K, Rb, Cs, Mg, Ca, Sr, Ba, In, Sn, Pb, Cu, Ag, Au, Zn, Cd, Hg, Cr, Mo, Mn, Fe, Co, Ni, Rn, Rh, Pd, Ir, Pt, Sb, Bi, as well as the group of the rare earth metals. Preferred metals are the alkaline and alkaline earth metals, Cu, Ag, Au, Fe, Co, Ni, Zn, Cd and Mn.

In a preferred embodiment of the invention, M is H$^\oplus$, $NH_4^\oplus$, an alkali metal cation or a primary, secondary, tertiary or quaternary ammonium cation of 1 to 24 carbon atoms.

The alkanol used as solvent contains 1 to 4, and, preferably, 1 to 3, carbon atoms. It may be substituted by methoxy or ethoxy. Representative examples of such alkanols are: methanol, ethanol, n- and isopropanol, n-, iso- and tert-butanol, methoxyethanol, ethoxyethanol, propoxyethanol, 1-methoxypropan-3-ol, 2-methoxypropan-1-ol. Preferred solvents are methanol, ethanol, 1- or 2-propanol and 2-methoxyethanol. It is also possible to use mixtures of the alkanols with one another or with ethers, such as diethyl ether or ethylene glycol dimethyl ether.

The salt of the organic carboxylic acid may be an ammonium or a metal salt, such as $NH_4^\oplus$, an ammonium cation of a primary, secondary or tertiary amine containing a total of 1 to 20 carbon atoms, an alkali metal salt or an alkaline earth metal salt. Alkali metal salts and ammonium salts are preferred. $NH_4^\oplus$ and Li$^\oplus$ salts are most preferred.

The organic carboxylic acid may be selected from mono-, di-, tri- or tetracarboxylic acids. Aliphatic, cycloaliphatic, aromatic and heterocyclic or heteroaromatic monocarboxylic acids which contain 1 to 18, preferably 1 to 12, carbon atoms, are preferred.

In a preferred embodiment of the invention, the organic acid has the formula (A)

$$R_a\text{—X—COOH} \qquad (A)$$

wherein X is a direct bond, $C_1$-$C_4$alkylene, $C_2$-$C_4$alkylidene or $C_2$-$C_4$alkenylene, $R_3$ is H, $C_1$-$C_{12}$alkyl, $C_2$-$C_{12}$alkenyl, $C_2$-$C_{12}$alkynyl, $C_3$-$C_{12}$cycloalkyl, $C_3$-$C_{12}$cycloalkenyl, $C_6$-$C_{16}$aryl, $C_3$-$C_{12}$heterocycloalkyl, $C_3$-$C_{12}$heterocycloalkenyl, $C_6$-$C_{16}$heteroaryl, which are unsubstituted or substituted by —OH, —SH, —CN, —NO$_2$, halogen, $C_1$-$C_6$alkyl, $C_1$-$C_6$alkoxy, $C_1$-$C_6$alkylthio, $C_1$-$C_6$alkyl—Y—, where Y is —CO—, —SO—, —SO$_2$—, —CO—O—, —O—CO—, —CO—NR$_b$R$_c$—, —NR$_b$R$_c$—CO—, and R$_b$ and R$_c$ are each independently of the other H, $C_1$-$C_6$alkyl, $C_2$-$C_4$hydroxyalkyl or R$_b$ and R$_c$, when taken together, are tetramethylene, pentamethylene or 3-oxapentyl-1,4-ene.

R$_a$ as alkyl, which may be linear or branched, is typically methyl, ethyl, n- and isopropyl, n- and isobutyl, pentyl, hexyl, heptyl, octyl, nonyl, decyl, undecyl and dodecyl.

R$_a$ as alkenyl, which may be linear or branched, is typically vinyl, crotonyl, allyl, but-1-en-1-yl, but-1-en-2-yl, but-1-en-3-yl, but-1-en-4-yl, but-2-en-1-yl, but-2- en-2-yl, but-2-en-4-yl, pentenyl, hexenyl, heptenyl, octenyl, nonenyl, decenyl, undecenyl and dodecenyl.

$R_a$ as alkynyl, which may be linear or branched, is typically ethynyl, prop-2-yn-1-yl, prop-2-yn-3-yl, butynyl, pentynyl, hexynyl, heptynyl, octynyl, decynyl and dodecynyl.

$R_a$ as cycloalkyl and cycloalkenyl preferably contains 4 to 8, most preferably 5 or 6, carbon atoms. Typical examples are cyclopropyl and cyclopropenyl, cyclobutyl and cyclobutenyl, cyclopentyl and cyclopentenyl, cyclohexyl and cyclohexenyl, cycloheptyl and cycloheptenyl, cyclooctyl and cyclooctenyl.

$R_a$ as aryl preferably contains 6 to 12 carbon atoms. Typical examples are phenyl, biphenyl and naphthyl.

$R_a$ as heterocycloalkyl and heterocycloalkenyl preferably contains 4 to 8, most preferably 4 to 6, ring carbon atoms. Preferred hetero atoms are those selected from the group consisting of O, S and $NR_d$, wherein $R_d$ is H, $C_1-C_6$alkyl or $C_1-C_7$acyl. $R_a$ as heteroaryl preferably contains 4 to 11 ring carbon atoms and, preferably, hetero atoms selected from the group consisting of O, S and —N=. Typical examples of heterocycles are pyrrolidine, tetrahydrofuran, tetrahydrothiophen, pyrroline, dihydrofuran, dihydrothiophene, indane, dihydrocoumarone, dihydrobenzothiophene, carbazole, dibenzofuran, dibenzothiophene, pyrazolidine, imidazolidine, pyrazoline, imidazoline, benzimidazolidine, oxazolidine, oxazoline, thiazolidine, thiazoline, isooxazolidine, isooxazoline, isothiazolidine, isothiazoline, benzoxazolidine, benzoisooxazolidine, benzothiazolidine, 1,2,3- or 1,2,4-triazolidine, 1,2,3- or 1,2,4-triazoline, 1,2,3-or 1,2,4-oxazolidine or -oxazoline, piperidine, di- and tetrahydropyridine, dihydro- and tetrahydropyran, di-and tetrahydrothiopyran, piperazine, dehydropiperazine, morpholine, thiomorpholine, 1,3- and 1,4-dioxan, 1,4-dithiane, azepane, 1,3-Dioxolan, 1,3-dithiolane, pyrrole, indole, imidazole, benzoimidazole, furan, thiophene, benzofuran, benzothiophene, carbazole, dibenzofuran, dibenzothiophene, oxazole, isooxazole, thiazole, isothiazole, benzoxazole, benzothiazole, pyridine, pyrimidine, pyrazine, pyridazine, quinoline, isoquinoline, acridine, chromene, chroman, pyran, thiapyran, phenazine, phenoxazine, phenolthiazine, purine.

Representative examples of X in formula A are methylene, ethylene, 1,2- or 1,3-propylene, 1,2-, 1,3- or 1,4-butylene, ethylidene, 1,1- or 2,2-propylidene, 1,1- or 2,2-butylidene, ethenylene, prop-1-en-1,3- or -1,2- or -2,3-ylene.

$R_b$ and $R_c$ as alkyl and hydroxyalkyl may be methyl, ethyl, n- or isopropyl, n-, iso- or tert-butyl, n-pentyl, n-hexyl, 2-hydroxyethyl, 2- or 3-hydroxypropyl, 2-, 3- or 4-hydroxybutyl. $R_d$ as acyl is typically acetyl, propionyl and phenacyl.

In a preferred embodiment of the invention, the salts are $Li^\oplus$ or $NH_4^\oplus$ salts of carboxylic acids selected from the group consisting of furan-2-carboxylic acid, benzoic acid, methylbenzoic acid, phenylacetic acid, cinnamic acid, sorbic acid or $C_2-C_8$-alkanecarboxylic acids.

The organic compound of non-salt character preferably contains 2 to 20, more particularly 2 to 16 and, most preferably, 2 to 12, carbon atoms. Most preferably the organic compound is an ester of an organic monocarboxylic acid containing a total of 2 to 16 carbon atoms, an ether containing 2 to 12 carbon atoms, a ketone containing 3 to 16 carbon atoms, or an alcohol containing 5 to 16 carbon atoms.

In a preferred embodiment of the invention, the organic compound is a $C_1-C_6$alkyl ester of furan-2-carboxylic acid, benzoic acid, methylbenzoic acid, phenylacetic acid, cinnamic acid, sorbic acid or a $C_2-C_{12}$alkanecarboxylic acid; a $C_5-C_{12}$alkanol or benzyl alcohol; a dialiphatic ketone of 3 to 10 carbon atoms, a $C_1-C_6$alkylphenyl ketone or diphenyl ketone; or a dialiphatic ether of 2 to 8 carbon atoms, a $C_1-C_6$alkylphenyl ether or diphenyl ether.

For carrying out the process of this invention the membrane can be of different shape and built into separating modules of conventional construction. Thus, for example, flat membranes or asymmetrical membranes can be combined to two- or multi-compartment systems. It is also possible to use tubular membranes or hollow fibres which are normally used in the form of bundles. To increase mechanical stability, the membranes can be mounted on a supporting frame. The membranes are prepared by known methods.

The process of the invention is normally carried out at room temperature. To attain a sufficient rate of flow it is advantageous to apply elevated pressure on the side of the solution. The pressure is preferably 1 to 10 MPa, most preferably 1 to 6 MPa. In a special embodiment of the invention, the process is carried out by the countercurrent principle.

The process of the invention may be used as concentration or purification process or for recovering or separating reaction components or by-products from reaction residues or reaction mixtures, or for isolating and purifying intermediates, especially when the substances in question are thermally labile.

The aromatic dicarboxylic acid radicals (a) can be radicals of mononuclear or binuclear aryldicarboxylic acids which preferably contain a total of 8 to 16 carbon atoms and which are unsubstituted or substituted by preferably F, Cl, Br or $NO_2$. The aromatic tricarboxylic acid radicals (b) can be radicals of mononuclear or binuclear aryltricarboxylic acids which preferably contain 9 to 17 carbon atoms and which are unsubstituted or substituted by preferably F, Cl, Br or $NO_2$.

The diamine radicals (c) and (d) are preferably mononuclear or binuclear aryl radicals which preferably contain 6 to 14 carbon atoms and which are unsubstituted or substituted by preferably F, Cl, Br methyl or ethyl.

The copolyamide or copolyimide-amide preferably contains 60 to 95 mol %, most preferably 75 to 95 mol %, of diamine radicals(c) and 5 to 40 mol %, most preferably 5 to 25 mol % of diamine radicals (d), based on said diamine radicals. The inherent viscosity of the copolyamides, copolyamide-imides or of the copolymers can be from 0.2 to 3.0 dl/g, preferably 0.3 to 2.0 dl/g and, most preferably, 0.3 to 1.2 dl/g.

In a preferred embodiment of the process of the invention, the copolyamide and/or copolyimide-amide comprises a) 60 to 95 mol % of at least one structural repeating unit of formulae I and/or Ia,

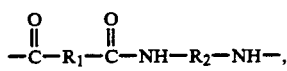

$$\overset{O}{\underset{\|}{-C}}-R_1-\overset{O}{\underset{\|}{C}}-NH-R_2-NH-, \quad (I)$$

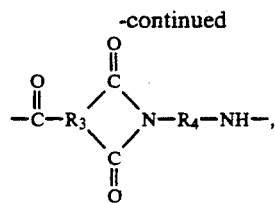

(Ia)

and b) 5 to 40 mol % of at least one structural repeating unit of formulae II and/or IIa,

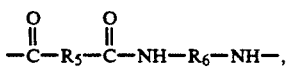

(II)

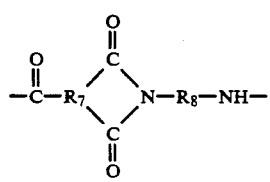

(IIa)

based on the copolymers, wherein $R_1$ and $R_5$ are each independently of the other a radical of formula

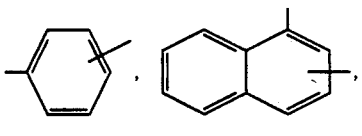

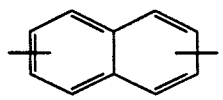

or

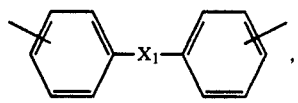

which radical is unsubstituted or substituted by Cl, Br, $NO_2$, $C_1$-$C_4$alkyl or $C_1$-$C_4$alkoxy, in which formulae $X_1$ is a direct bond, $CH_2$, $-(CH_2)_2-$, $-HC=CH-$,

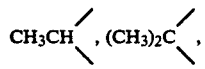

$-NR_9-$, $-N=N-$, $-CO-$, $-O-$, $-S-$, $-SO-$ or $-SO_2-$, and $R_9$ is H or $C_1$-$C_6$alkyl, $R_3$ and $R_7$ are each independently of the other a radical of formulae

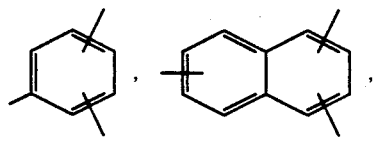

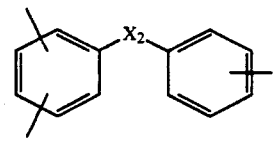

wherein two bonds are linked to two adjacent carbon atoms, and $X_2$ independently has the same meaning as $X_1$, $R_2$ and $R_4$ are each independently of the other an unsubstituted or chloro-, bromo- or $C_1$-$C_4$alkyl-substituted radical of formulae

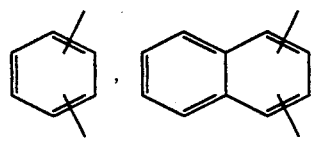

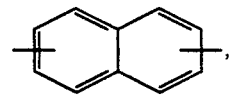

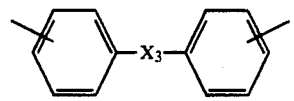

wherein $X_3$ independently has the same meaning as $X_1$, and $R_6$ and $R_8$ are each independently of the other a radical of formulae

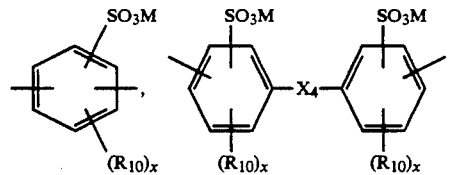

wherein $X_4$ independently has the same meaning as $X_1$, $R_{10}$ is $C_1$-$C_4$alkyl, x is 0, 1, 2 or 3 and M is $H^\oplus$, $NH_4^\oplus$, an alkali metal cation or a primary, secondary, tertiary or quaternary ammonium cation of 1 to 24 carbon atoms.

$X_1$, $X_2$, $X_3$ and $X_4$ are each independently of one another a direct bond $-CH_2-$, $-CO-$, $-S-$ or $-O-$.

Exemplary of aromatic dicarboxylic acids from which the radicals $R_1$ and $R_5$ are derived are terephthalic acid, isophthalic acid, 4-nitroisophthalic acid, 4-chloroisophthalic acid, tetrabromoterephthalic acid, 4,4'-, 3,4'- or 3,3'-diphenylmethanedicarboxylic acid, or 3,4'- or 3,3'-diphenyldicarboxylic acid, or 3,4'- or 3,3'-diphenylether dicarboxylic acid, or 3,4'- or 3,3'-diphenylsulfonedicarboxylic acid, or 3,4'- or 3,3'-benzophenonedicarboxylic acid, 1,3-, 1,4-, 2,6- or 2,7-naphthalenedicarboxylic acid. Further suitable aromatic dicarboxylic acids containing benzophenone units are disclosed, for example, in EP-A-0198798.

Preferred dicarboxylic acids are terephthalic and isophthalic acid which may be substituted by F, Cl, Br or $NO_2$, 4,4'-benzophenonedicarboxylic acid, 4,4'- diphenyldicarboxylic acid, 4,4'-diphenylmethanedicarboxylic acid, 4,4'-diphenyl ether dicarboxylic acid, and 4,4'-diphenylsulfonedicarboxylic acid.

Exemplary of aromatic tricarboxylic acids from which $R_3$ and $R_7$ are derived are trimellitic acid, 1,6,7- or 2,6,7-naphthalenetricarboxylic acid, 3,4,4'-diphenyltricarboxylic acid, or 3,4,4'-diphenylmethanetricarboxylic acid, or 3,4,4'-diphenyl ether tricarboxylic acid, or 3,4,4'-diphenylthioether tricarboxylic acid, or 3,4,4'-diphenylsulfonetricarboxylic acid, or 3,4,4'-benzophenonetricarboxylic acid. The preferred tricarboxylic acid is trimellitic acid.

Examples of aromatic diamines from which $R_2$ and $R_4$ are derived are described in EP-A-0 138 768. Representative examples are: m- or p-phenylenediamine, 4-chloro-m-phenylenediamine, 3-chloro-p-phenylenediamine, mono- to tetramethylsubstituted m- or p-phenylenediamines; 1,3-, 2,6- or 2,7-naphthylenediamines which may be substituted by Cl, methyl or ethyl; or diamines of formula B

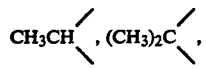   (B)

wherein the NH$_2$ groups are in m- or p-position to the X$_3$ group, X$_3$ is a direct bond, —CH$_2$—,

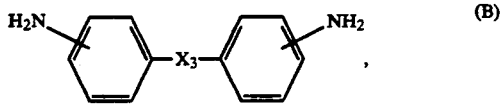

—O—, —S—, —SO$_2$— or —CO—, and the benzene rings may preferably be substituted by methyl or ethyl, preferably in one or both o-positions to the NH$_2$ group. Preferred diamines are m- and p-phenylenediamine, 4-chloro-m-phenylenediamine, 4,4'-diamino-3,3'-dimethyldiphenylmethane, 4,4'-diamino-3,3',5,5'-tetramethyldiphenylmethane, 4,4'-diamino-2,2',6,6'-tetramethyldiphenylmethane.

The diamines from which the radicals $R_6$ and $R_8$ are derived may be the same diamines as indicated for $R_2$ and $R_4$, but they additionally contain a SO$_3$M group or one substituent is replaced by a SO$_3$M group. The SO$_3$M group is preferably in the m-positions to the amino groups. Typical examples are (only given as sulfonic acids): 3,5-diaminobenzene-1-sulfonic acid, 3,5-diamino-2-methyl- or 4-methylbenzene-1-sulfonic acid, 3,5-diamino-2,4-dimethyl- or 2,6-dimethylbenzenesulfonic acid, 3,5-diamino-2,4,6-trimethylbenzene-1-sulfonic acid, 3,6- or 3,7-diaminonaphthalene-1-sulfonic acid, 3,3'-diaminodiphenyl-5,5'-disulfonic acid, 3,3'-diamino-4,4'-dimethyldiphenyl-5,5'-disulfonic acid, 3,3'-diamino-2,2',4,4'-tetramethyl-diphenyl-5,5'-disulfonic acid, 4,4'-diaminodiphenyl-2,2'-disulfonic acid, 4,4'-diamino-3,3'- or -5,5'-dimethyldiphenyl-2,2'-disulfonic acid, 4,4'-diamino-3,3',5,5'-tetramethyldiphenyl-2,2'-disulfonic acid, as well as corresponding diphenylmethanedisulfonic acid, diphenyl ether disulfonic acid, diphenyl thioether disulfonic acid, diphenylsulfonedisulfonic acid and benzophenonediaminodisulfonic acid.

In a preferred embodiment of the process of this invention, the copolyamide is one comprising structural units of formulae I and II, and $X_1$ and $X_4$ are each independently of the other a direct bond, —CH$_2$—, —CO—, —O— or —S—.

In another preferred embodiment of the process, in the structural units of formula II of the copolyamide $R_1$ and $R_5$ are each independently of the other m- and/or p-phenylene which are unsubstituted or substituted by —NO$_2$—, —Cl or —Br, $R_2$ is unsubstituted phenylene or phenylene which is substituted by —Cl, —Br, methyl or ethyl, or is 3,3'- or 4,4'-diphenylmethanediyl which is substituted in both o-positions to the amino groups by methyl and/or ethyl, and $R_6$ is a radical of formulae

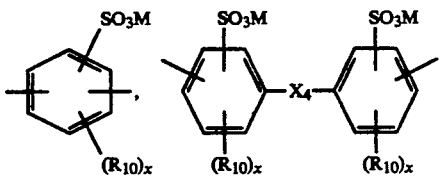

wherein $X_4$ is a direct bond or —CH$_2$—, $R_{10}$ is methyl or ethyl, x is 1, 2 or 3, and M is H$^\oplus$, NH$_4^\oplus$, Li$^\oplus$, Na$^\oplus$, K$^\oplus$, Rb$^\oplus$, Cs$^\oplus$ or quaternary ammonium of 4 to 16 carbon atoms.

In a particularly preferred embodiment of the process of the invention, $R_4$ is a radical of formula

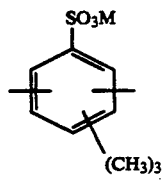

wherein M is H$^\oplus$, NH$_4^\oplus$, Li$^\oplus$, Na$^\oplus$, K$^\oplus$, Rb$^\oplus$, Cs$^\oplus$ or quaternary ammonium of 4 to 16 carbon atoms.

The preparation of the copolyamides and copolyimide-amides is carried out in known manner for the membranes used in the process of the invention. The monomers are either known or they can be prepared by known processes. The membranes are prepared by known methods, for example by the sheet casting method.

In EP-A-0 138 768 and EP-A-0 198 798 there are disclosed radiation-sensitive polyamides and polyimide-amides which contain diamine radicals carrying alkyl groups in the o-positions to the amino groups and radicals of dicarboxylic acids containing benzophenone groups. These polymers are only soluble in polar and aprotic organic solvents and, after irradiation through a photomask, development can only be effected with organic solvents—a disadvantageous procedure from the environmental aspect.

Surprisingly, it has been found that copolyamides and copolyimide-amides of aromatic dicarboxylic or tricarboxylic acids and aromatic diamines carrying alkyl groups in the o-positions to the amino groups and aromatic diamines containing SO$_3$M groups are radiation-sensitive, and are soluble and can be developed in polar and aprotic solvents and in aqueous basic media. The mechanical stability and solvent resistance of membranes for the separation process of this invention made from such polymers can be enhanced by irradiation.

The invention further relates to copolymers which are selected from the group of the copolyamides and copolyimide-amides having an inherent viscosity of 0.2 to 3.0 dl/g, measured at 25° C. in a solution of 0.5% by weight of copolymer in N-methylpyrrolidone, and which comprise, based on the copolymer:

a) 10 to 95 mol % of at least one structural repeating unit of formulae III and/or IIIa $$-\overset{O}{\overset{\|}{C}}-R_{11}-\overset{O}{\overset{\|}{C}}-NH-R_{12}-NH-, \qquad (III)$$

$$-\overset{O}{\overset{\|}{C}}-R_{13}\overset{\overset{O}{\overset{\|}{C}}}{\underset{\underset{O}{\overset{\|}{C}}}{\diagdown}}N-R_{14}-NH-, \qquad (IIIa)$$

and b) 5 to 90 mol % of at least one structural repeating unit of formulae IV and/or IVa $$-\overset{O}{\overset{\|}{C}}-R_{15}-\overset{O}{\overset{\|}{C}}-NH-R_{16}-NH-, \qquad (IV)$$

$$-\overset{O}{\overset{\|}{C}}-R_{17}\overset{\overset{O}{\overset{\|}{C}}}{\underset{\underset{O}{\overset{\|}{C}}}{\diagdown}}N-R_{18}-NH- \qquad (IVa)$$

wherein $R_{11}$ and $R_{15}$ are each independently of the other divalent radicals of a mononuclear or binuclear aromatic dicarboxylic acid of 8 to 20 carbon atoms, which radicals are each unsubstituted or substituted by halogen, nitro, $C_1$-$C_4$alkyl or $C_1$-$C_4$alkoxy, $R_{13}$ and $R_{17}$ are each independently of the other trivalent radicals of a mononuclear or binuclear aromatic tricarboxylic acid of 8 to 20 carbon atoms, which radicals are each unsubstituted or substituted by halogen or nitro, $R_{12}$ and $R_{14}$ are each independently of the other a radical of formula

[structures: phenyl with $(R_{19})_y$, or two phenyl rings with $(R_{19})_y$ linked by $X_5$]

wherein $R_{19}$ is $C_1$-$C_4$alkyl, $X_5$ is a direct bond, —CH₂—, $-(CH_2)_2-$, —HC=CH—, $$CH_3CH\diagup_{\diagdown}, \; (CH_3)_2C\diagup_{\diagdown},$$

—NR₉—, —N=N—, —CO—, —O— or —S— and R₉ is H or $C_1$-$C_6$alkyl, y is 0, 1, 2, 3 or 4 and $R_{16}$ and $R_{18}$ are each independently of the other a radical of formula

[structures: phenyl with SO₃M and $(R_{19})_x$, or two phenyl rings with SO₃M and $(R_{19})_x$ linked by $X_6$]

wherein $R_{19}$ is $C_1$-$C_4$alkyl, x is 0, 1, 2 or 3, $X_6$ is a direct bond, —CH₂—, $-(CH_2)_2-$, —HC=CH—, $$CH_3CH\diagup_{\diagdown}, \; (CH_3)_2C\diagup_{\diagdown},$$

—NR₉—, —N=N—, —CO—, —O—, —S—, —SO— or —SO₂— and R₉ is H or $C_1$-$C_6$alkyl, and M is H⊕, NH₄⊕, a monovalent metal cation or an organic ammonium cation of 1 to 30 carbon atoms, with the proviso that, in at least one of the radicals $R_{12}$, $R_{14}$, $R_{16}$ and $R_{18}$, at least two radicals $R_{19}$ are in the ortho-positions of the free bonds.

Preferably y is 2, 3 or 4. In addition, x is preferably 2 or 3. $R_{19}$ is preferably ethyl and, most preferably, methyl. In a preferred embodiment of the invention, y is 2, 3 or 4 and x is 2 or 3 and a pair of radicals $R_{19}$ are preferably in both o-positions to the free bond.

The copolymers preferably comprise 60 to 95 mol % of structural units of formulae III and/or IIIa and 5 to 40 mol % of structural units of formulae IV and/or IVa.

Suitable aromatic dicarboxylic and tricarboxylic acids have been previously mentioned. Preferred copolymers are those wherein $R_{11}$ and $R_{15}$ are each independently of the other a radical of formula

[structures: phenyl, naphthyl, naphthyl, or two phenyls linked by $X_1$]

which radical is unsubstituted or substituted by Cl, Br or NO₂, wherein $X_1$ is a direct bond, CH₂, $-(CH_2)_2-$, —HC=CH—, $$CH_3CH\diagup_{\diagdown}, \; (CH_3)_2C\diagup_{\diagdown},$$

—NR₉—, —N=N—, —CO—, —O—, —S—, —SO— or —SO₂—, and R₉ is H or $C_1$-$C_6$alkyl, and $R_{13}$ and $R_{17}$ are each independently of the other a radical of formula

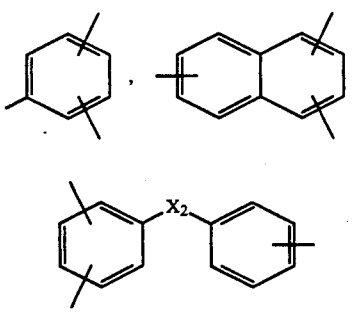

wherein two bonds are attached to two adjacent carbon atoms and $X_2$ independently has the same meaning as $X_1$.

In a preferred embodiment of the invention $R_{11}$ and $R_{15}$ are each independently of the other unsubstituted o-, m- or p-phenylene or o-, m- or p-phenylene which is substituted by Cl, Br or $NO_2$, or a radical of formula

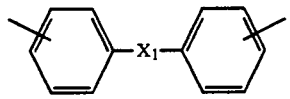

wherein the free bonds are in m- or p-position to the group $X_1$, and $X_1$ is a direct bond, $-CH_2-$, $-O-$, $-S-$, $-SO_2-$ or $-CO-$.

M is preferably $H^\oplus$, $NH_4^\oplus$, an alkali metal cation or a primary, secondary, tertiary or quaternary ammonium cation of 1 to 24 carbon atoms.

$R_{19}$ is preferably methyl or ethyl.

$R_{12}$ and $R_{14}$ are preferably each independently of the other a radical of formula

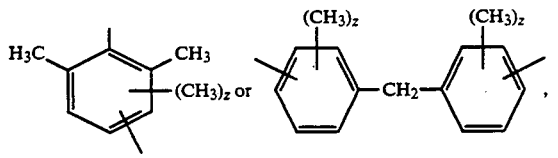

wherein in the first formula z is 0, 1 or 2 and the free bonds are in m- or p-position to each other, and in the second formula the free bonds are in m- or p-position to the $CH_2$ group, and the two $CH_3$ groups are each in the ortho-positions of the free bonds.

$R_{16}$ and $R_{18}$ are preferably each independently of the other a radical of formula

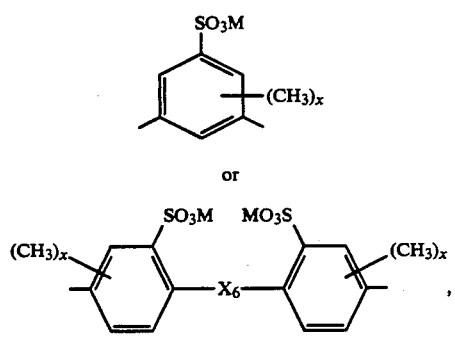

wherein x is 0, 1, 2 or 3, $X_6$ is a direct bond, $-CH_2-$, $-O-$, $-S-$, $-CO-$ or $-SO_2-$, and M is $H^\oplus$, $NH_4^\oplus$, an alkali metal cation or primary, secondary, tertiary or quaternary ammonium of 1 to 24 carbon atoms.

In a particularly preferred embodiment of the invention the copolyamide is one containing structural repeating units of formula

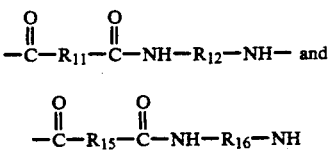

wherein $R_{11}$ and $R_{15}$ are each independently of the other unsubstituted m- or p-phenylene or m- or p-phenylene which is substituted by Cl, Br or nitro, or

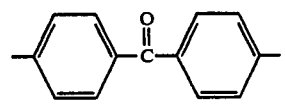

$R_{12}$ is a radical of formula

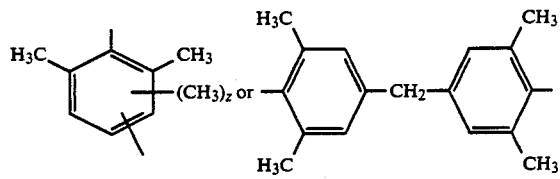

wherein z is 0, 1 or 2, and $R_{16}$ is a radical of formula

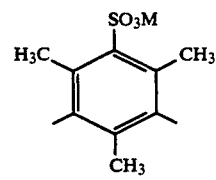

wherein M is $H^\oplus$, $NH_4^\oplus$, an alkali metal cation or primary, secondary, tertiary or quaternary ammonium of 1 to 24 carbon atoms.

The invention further relates to a process for the preparation of the novel copolymers, which comprises reacting, based on the copolymer, a) 50 mol % of at least one dicarboxylic acid of formulae V and/or Va

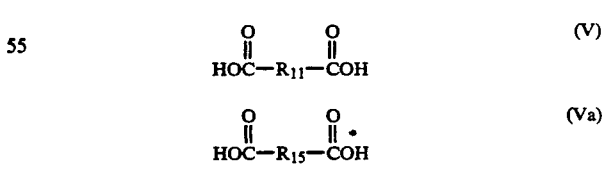

and/or at least one tricarboxylic acid of formulae VI and/or VIa $R_{13}-(COOH)_3$ (VI)

$R_{17}-(COOH)_3$ (VIa)

or polyamide forming derivatives thereof, with b) 5 to 47.5 mol % of at least one diamine of formulae VII and/or VIIa

 (VII)

 (VIIa)

and c) 2.5 to 45 mol % of at last one diamine of formulae VIII and/or VIIIa

 (VIII)

 (VIIIa)

The monomers used in the process of the invention are known and some are commercially available.

Suitable polyamide forming derivatives are typically the acid anhydrides, acid amides, acid halides and acid esters. Suitable processes include solvent polymerisation, melt condensation and interfacial polycondensation. Suitable solvents are cited below.

The reaction temperatures depend essentially on the starting materials, the preparatory processes and the reactivity thereof. They may be in the range from $-50°$ to $350°$ C., preferably from $50°$ to $300°$ C. The polycondensation can also be carried out under normal pressure or partial vacuum. Water, alcohol or amine formed in the course of the condensation is conveniently removed from the reaction mixture, and hydrohalides such as HCl or HBr are neutralised by suitable agents, such as tertiary amines or epoxides.

The novel copolymers are polymers which can be crosslinked direct by irradiation. They are suitable for making sheets, fibres and for coating substrates, for surface protection or for producing relief images, and the properties of the polycondensates can be modified by irradiation. The high melting aromatic copolymers are preferably processed from solution.

A preferred field of use is that of coating surfaces and producing relief images on such coated surfaces, to which utility the invention also relates. It is especially advantageous that, for attaining the desired properties, the novel copolymers can be correspondingly adapted for specific requirements by the choice of different monomers and/or by blending different copolymers. A further particular advantage of the novel polymers is their solubility in aqueous basic media, for example in aqueous solutions of alkali metal hydroxides (NaOH, KOH), or in aqueous solutions of alkali metal carbonates (NaHCO$_3$, Na$_2$CO$_3$, K$_2$CO$_3$).

The invention further relates to a coated material containing on a support a layer of a novel copolymer, wherein X$_5$ may additionally be —SO— or —SO$_2$—.

To prepare the coated material, a copolymer or a mixture thereof is dissolved preferably in a suitable organic solvent, with or without heating. Suitable solvents are polar aprotic solvents which may be used by themselves or as mixtures of at least two solvents. Typical examples of such solvents are: ethers such as dibutyl ether, tetrahydrofuran, dioxane, ethylene glycol, dimethyl ethylene glycol, dimethyl diethylene glycol, diethyl diethylene glycol, dimethyl triethylene glycol, halogenated hydrocarbons such as methylene chloride, chloroform, 1,2-dichlorethane, 1,1,1-trichloroethane, 1,1,2,2-tetrachloroethane, carboxylates and lactones such as ethyl acetate, methyl propionate, ethyl benzoate, 2-methoxyethylacetate, γ-butyrolactone, o-valerolactone and pivalolactone, carboxamides and lactams such as formamide, acetamide, N-methylformamide, N,N-dimethylformamide, N,N-dimethylformamide, N,N-dimethylacetamide, N,N-diethylacetamide, γ-butyrolactam, ε-caprolactam, N-methylpyrrolidone, N-acetylpyrrolidone, N-methylcaprolactam, tetramethylurea, hexamethylphosphoric triamide, sulfoxides such as dimethyl sulfoxide, sulfones such as dimethyl sulfone, diethyl sulfone, trimethylene sulfone, tetramethylene sulfone, trimethylamine, triethylamine, N-methylpyrrolidine, N-methylpiperidine, N-methylmorpholine, substituted benzenes such as chlorobenzene, nitrobenzene, phenols or cresol.

Undissolved constituents can be removed by filtration, preferably pressure filtration. The concentration of polymer in the coating material obtained is preferably not more than 50% by weight, more particularly not more than 30% by weight and, most preferably, not more than 20% by weight, based on the solution.

During the preparation of the solutions it is possible to add further customary modifiers which do not adversely affect the light sensitivity. Typical examples of such modifiers are: delustrants, levelling agents, finely particulate fillers, flame retardants, fluorescent whitening agents, antioxidants, light stabilisers, dyes, pigments and adhesion promoters. If desired, sensitisers may also be added, typically thioxanthone derivatives or benzophenone derivatives, so as to enhance the light sensitivity still further.

The coating composition can be applied to suitable substrates and carrier materials by conventional methods such as dip coating, brushing and spraying, whirl coating, cascade coating and curtain coating. Suitable substrates include plastics, metals and metal alloys, semi-metals, semi-conductors, glass, ceramics and other inorganic materials such as SiO$_2$ and Si$_3$N$_4$. The solvent may subsequently be removed by heating and under vacuum. Tack-free, dry and uniform films are obtained. Depending on the use, the films may have thicknesses up to c. 500 μm and more, preferably from 0.5 to 500 μm and, most preferably, from 1 to 50 μm.

The radiation-sensitive layer in the material of this invention can be crosslinked by irradiation.

The photostructuring or photocrosslinking can be effected by high-energy radiation, typically by light, preferably in the UV range, by X-rays, laser light, electron beams and the like. The material of this invention is admirably suitable for producing protective films, passivation coatings, and as photographic recording material for heat-stable relief images.

The invention further relates to this utility. Fields of use include protective, insulating and passivation coatings in electrotechnology and electronics, photomasks for electronics, textile printing and the graphics industry, etch resists for making printed circuits and printing plates and integrated circuits, relays for making X-ray masks, as solder varnish, as dielectric for multilayer circuits, as structural element for liquid crystal displays.

Protective films are produced by direct irradiation, the exposure times depending essentially on the layer thicknesses and the light-sensitivity.

Photographic production of the relief structure is effected by imagewise exposure through a photomask and subsequent development by removing unexposed areas with an aqueous alkaline medium, preferably an aqueous solution of an alkali metal hydroxide (NaOH, KOH) or an aqueous solution of an alkali metal carbonate (Na$_2$CO$_3$, K$_2$CO$_3$, KHCO$_3$, NaHCO$_3$), after which the image produced may be stabilised by a thermal aftertreatment.

The invention further relates to a process for producing protective coatings or relief images, which comprises irradiating the layer of the material over the surface or through a photomask and thereafter developing the image in an aqueous alkaline medium by dissolving out the unexposed areas.

The polymer layer of the material of this invention has a light-sensitivity sufficient for many end uses and in some cases is high, and it can be photocrosslinked direct. The protective films and relief images are distinguished by good adhesion and by heat resistance, mechanical strength and resistance to chemicals. Only insignificant contraction is observed in thermal aftertreatments. In addition, the use of modifiers for inducing or increasing light-sensitivity can be avoided. The material is storage stable, but must be protected from the action of light.

The invention is illustrated in more detail by the following Examples.

A) Preparation of the Copolymers

EXAMPLES A1-A15

The diamines, dissolved in N-methylpyrrolidone (NMP), are charged to a 200 ml glass flask fitted with stirrer, reflux condenser, dropping funnel, drying tube and cooling bath. The solution is cooled to 15° C. and propylene oxide is added. With efficient stirring, the dicarboxylic acid chlorides are added dropwise over 15 minutes. The solution is stirred for a further 3 hours at 15°–20° C. Then the copolymer is precipitated by addition of methanol, the precipitate is isolated by filtration and dried under a high vacuum at 40° C. Further particulars will be found in Table 1.

TABLE 1

| Ex. | Diamine 1 (mmol) | Diamine 2 (mmol) | 1. Dicarbonyl dichloride (mmol) | 2. Dicarbonyl dichloride (mmol) | NMP[1] (amount in g) | PPO[2] (amount in g) | Inherent[3] viscosity (dl/g) |
|---|---|---|---|---|---|---|---|
| A1 | 4,4'-diamino-3,5,3',5'-tetramethyldiphenylmethane (22.5) | 3,5-diamino-2,4,6-trimethylbenzene-1-sulfonic acid tetrabutylammonium salt (2.5) | isophthaloyl dichloride (7.5) | terephthaloyl dichloride (17.5) | 78 | 12 | 0.89 |
| A2 | 4,4'-diamino-3,5,3',5'-tetramethyldiphenylmethane (13.5) | 3,5-diamino-2,4,6-trimethylbenzene-1-sulfonic acid tetrabutylammonium salt (1.5) | 4-nitro-isophthaloyl dichloride (7.5) | terephthaloyl dichloride (7.5) | 62 | 8 | 0.69 |
| A3 | 4,4'-diamino-2,6,2',6'-tetramethyldiphenylmethane (12.9) | 3,5-diamino-2,4,6-trimethylbenzene-1-sulfonic acid tetrabutylammonium salt (1.5) | isophthaloyl dichloride (4.3) | terephthaloyl dichloride (10.1) | 75 | 5 | 0.31 |
| A4 | p-phenylenediamine (16.0) | 3,5-diamino-2,4,6-trimethylbenzene-1-sulfonic acid tetrabutylammonium salt (4.0) | isophthaloyl dichloride (6.0) | terephthaloly dichloride (14.0) | 120 | 7 | 0.85 |
| A5 | 4-chloro-m-phenylenediamine (18.0) | 3,5-diamino-2,4,6-trimethylbenzene-1-sulfonic acid tetrabutylammonium salt (2.0) | isophthaloyl dichloride (6.0) | terephthaloyl dichloride (14.0) | 42 | 12 | 0.60 |
| A6 | 4-chloro-m-phenylenediamine (13.5) | 3,5-diamino-2,4,6-trimethylbenzene-1-sulfonic acid tetrabutylammonium salt (1.5) | 4-nitro-isophthaloyl dichloride (7.5) | terephthaloyl dichloride (7.5) | 72 | 8 | 0.39 |
| A7 | 4,4'-diamino-trans-stilbene-2,2'-disulfonic acid di-tetrabutylammonium salt (2.0) | 4,4'-diamino-3,3'-diethyl-5,5'-dimethyl-diphenylmethane (8.0) | isophthaloyl dichloride (3.0) | terephthaloyl dichloride (7.0) | 80 | 3.5 | 0.690 |
| A8 | 4,4'-diamino-diphenyl-2,2'-disulfonic acid di-tetrabutylammonium salt (0.5) | 4,4'-diamino-3,3'-diethyl-5,5'-dimethyl-diphenylmethane (9.5) | isophthaloyl dichloride (3.0) | terephthaloyl dichloride (7.0) | 80 | 3.5 | 0.482 |
| A9 | 4,4'-diamino-trans-stilbene-2,2'-disulfonic acid di-tetra-butyl-ammonium salt (0.5) | 2,4,6-trimethyl-m-phenylenediamine (9.5) | isophthaloyl dichloride (9.0) | diethylmalonyl dichloride (1.0) | 80 | 3.5 | 0.167 |
| A10 | 4,4'-diamino-trans-stilbene-2,2'-disulfonic acid di-tetrabutylammonium salt (0.5) | 3,3'-5,5'-tetramethylbenzidine (9.5) | isophthaloyl dichloride (3.0) | terephthaloyl dichloride (7.0) | 80 | 3.5 | 1.257 |
| A11[4] | 3,5-diamino-2,4,6-trimethylbenzene-1-sulfonic acid tetra- | 2,4,6-trimethyl-m-phenylenediamine (1.0) | isophthaloyl dichloride (3.0) | diethylmalonyl dichloride (7.0) | 80 | 3.5 | 0.460 |

TABLE 1-continued

| Ex. | Diamine 1 (mmol) | Diamine 2 (mmol) | 1. Dicarbonyl dichloride (mmol) | 2. Dicarbonyl dichloride (mmol) | NMP[1] (amount in g) | PPO[2] (amount in g) | Inherent[3] viscosity (dl/g) |
|---|---|---|---|---|---|---|---|
| | butylammonium salt (8.0) | | | | | | |
| A12 | 3,5-diamino-2,4,6-trimethylbenzene-1-sulfonic acid tetrabutylammonium salt (1.0) | 2,4,6-trimethyl-m-phenylenediamine (9.0) | isophthaloyl dichloride (9.0) | trans-3,6-endo-methylene-1,2,3,6-tetrahydrophthaloyl dichloride (1.0) | 80 | 3.5 | 0.249 |
| A13 | 3,5-diamino-2,4,6-trimethylbenzene-1-sulfonic acid tetrabutylammonium salt (1.0) | 2,4,6-trimethyl-m-phenylenediamine (9.0) | terephthaloyl dichloride (7.0) | trans-3,6-endo-methylene-1,2,3,6-tetrahydrophthaloyl dichloride (3.0) | 80 | 3.5 | 0.246 |
| A14[5] | 4,4'-diamino-trans-stilbene-2,2'-disulfonic acid di-tetrabutylammonium salt (0.5) | 4,4'-diamino-3,3'-diethyl-5,5'-dimethyldiphenylmethane (9.5) | isophthaloyl dichloride (2.9) | 4,4'-stilbene-dicarbonyl dichloride (0.5) | 80 | 3.5 | 0.249 |
| A15 | 4,4'-diamino-trans-stilbene-2,2'-disulfonic acid di-tetrabutylammonium salt (0.5) | 4,4'-diamino-3,3'-diethyl-5,5'-dimethyldiphenylmethane (9.5) | tetrachloro-terephthaloyl dichloride (3.0) | terephthaloyl dichloride (7.0) | 80 | 3.5 | 0.192 |

[1] NMP: N-methylpyrrolidone
[2] PPO: propylene oxide
[3] inherent viscosity: 0.5% by weight in NMP, 25° C.
[4] 3. diamine: 1.0 mmol % 2,4-diaminobenzoic acid
[5] 3. dicarbonyl dichloride: 6.6 mmol % terephthaloyl dichloride

B) Permeation Experiments

EXAMPLES B1 TO B8:

The membrane (diameter 4.7 cm, thickness 25 μm) is secured in a support in the centre of a pressure cell. Each compartment is connected to a reservoir for the solution or pure solvent to which a pump is connected. Conductivity cells are positioned between reservoirs and pumps, and UV detectors are positioned between outlet and reservoirs. A pressure of 2.5 MPa is applied on the side with the solution and a pressure of 0.3 MPa on the side with the solvent, and both the solution and the solution circulate in the same direction. The detectors measure the conductivity and UV absorption continuously. The data are evaluated by means of a computer program. The detectors are calibrated with the organic compound (methyl cinnamate) and with the salt of the carboxylic acid (lithium salt of cinnamic acid), and the calibration curves are converted into algorithms from which the desired data are computed. Methanol is used as solvent and the UV detection is carried out at 305 nm. The temperature is 25° C.

The selectivity is defined as follows, $G^P$ being the amount by weight in the permeate and $G^L$ the amount by weight in the solution:

$$S = \frac{G^P(\text{nonpolar organic compound})/G^P(\text{salt of the carboxylic acid})}{G^L(\text{nonpolar organic compound})/G^L(\text{salt of the carboxylic acid})}$$

Further particulars are given in Table 2.

TABLE 2

| | | | Amounts at start of experiment[1] | | Duration | Permeated amounts at conclusion of experiment | | |
|---|---|---|---|---|---|---|---|---|
| Ex. | Copolyamide of Example | Permeation rate (mg · min$^{-1}$ · cm$^{-2}$) | methyl cinnamate (mg) | Li cinnamate (mg) | of experiment (min) | methyl cinnamate (mg) | Li cinnamate (mg) | Selectivity |
| B1 | A1 | 0.285 | 25 | 25 | 3060 | 1.00 | 0.25 | 3.95 |
| B2 | A2 | 0.339 | 25 | 25 | 3060 | 0.94 | 0.11 | 8.52 |
| B3 | A4 | 1.766 | 25 | 25 | 1680 | 3.25 | 1.17 | 2.78 |
| B4 | A5 | 0.273 | 25 | 25 | 3780 | 0.96 | 0.50 | 1.11 |
| B5 | A6 | 0.160 | 25 | 25 | 5040 | 0.23 | 0.10 | 2.28 |
| B6 | A7 | 2.174 | 25 | 25 | 1020 | 2.05 | 0.24 | 8.54 |
| B7 | A8 | 0.057 | 25 | 25 | 7050 | 0.48 | 0.27 | 1.77 |
| | | 0.057 | 75[2] | 75[3] | 2520 | 1.98[2] | 0.11[3] | 18.00 |
| B8 | A10 | 0.446 | 75[2] | 75[3] | 2040 | 7.23[2] | 0.22[3] | 32.86 |

[1] 0.005% by weight of
[2] dimethyl phthalate
[3] 35% of the trilithium salt of trimellitic acid and 65% of the dilithium salt of trimellitic acid C) Exposure Example

EXAMPLE C1

A copolyamide prepared from 13.5 parts by weight of 4,4'-diamino-3,3',5,5'-tetramethyldiphenylmethane, 1.5 parts by weight of 3,5-diamino-2,4,6-trimethylbenzene-1-sulfonic acid tetra-n-butylammonium salt, 7.5 parts by weight of terephthaloyl dichloride and 7.5 parts of 4-nitroisophthaloyl dichloride is dissolved in N-methylpyrrolidone (10% by weight) and a copper laminate is coated with this solution with a 12μ cable (spin-coating) and dried at 100° C. The coating is then exposed through a photomask (Stouffer wedge) for 180 seconds at an intensity of 40 mW/cm² (lamp: Ultralux 5000H, distance 70 cm). Development is then carried out with 2N NaOH. The Stouffer step 6 is still clearly imaged.

What is claimed is:

1. A process for concentrating or separating salts of organic mono-, di, tri or tetracarboxylic acids from organic compounds of non-salt character with the aid of a semipermeable membrane, said organic compounds of non-salt character being selected from the group consisting of esters of carboxylic acids containing a total of 2 to 16 carbon atoms, ethers containing 2 to 12 carbon atoms, ketones containing 3 to 16 carbon atoms, and alcohols containing 5 to 16 carbon atoms, which process comprises contacting a solution of the salts and organic compounds in an in a substantially anhydrous solution of unsubstituted or $C_1$-$C_3$alkoxy substituted $C_1$-$C_4$alkoxy substituted $C_1$-$C_4$alkanol, mixtures of such alkanols or mixtures of such alkanols with ethers, with one side of the membrane, the pure solvent being present on the other side of the membrane, and said membrane is made from a copolyamide or copolyamide-amide of (a) at least one aromatic dicarboxylic acid radical of 8 to 20 carbon atoms and/or (b) at least one trivalent aromatic tricarboxylic acid radical of 9 to 20 carbon atoms, each of which radicals is unsubstituted or substituted by halogen, nitro, $C_1$-$C_4$alkyl or $C_1$-$C_4$alkoxy, (c) at least one first divalent and/or trivalent mononuclear or binuclear aromatic diamine radical and (d) at least one second divalent and/or trivalent aromatic mononuclear or binuclear diamine radical containing at least one —$SO_3M$ group, each of which radicals is unsubstituted or substituted by halogen or $C_1$-$C_4$alkyl, and M is $H^\oplus$, a mono- to trivalent metal cation, $NH_4^\oplus$ or an organic ammonium cation of 1 to 30 carbon atoms, whereby the compounds of non-salt character are concentrated or separated in the permeate.

2. A process according to claim 1, wherein the concentration of salts and organic compounds is 0.0001 to 10% by weight, based on the solution.

3. A process according to claim 1, wherein the thickness of the membrane is from 5 to 300 μm.

4. A process according to claim 1, wherein the solvent is methanol, ethanol, 1- or 2-propanol or 2-methoxyethanol.

5. A process according to claim 1, wherein the salts of the organic carboxylic acid are ammonium or metal salts.

6. A process according to claim 1, wherein the organic carboxylic acid is selected from the group consisting of aliphatic, cycloaliphatic, aromatic, heterocyclic and heteroaromatic monocarboxylic acids of 1 to 18 carbon atoms.

7. A process according to claim 1, which is carried out at room temperature.

8. A process according to claim 1, wherein a pressure of 1 MPa to 10 MPa is applied on the side of the solution.

9. A process according to claim 1, which is carried out in countercurrent.

10. A process according to claim 1, wherein the copolyamide or copolyimide-amide contains 60 to 95 mol % of diamine radicals (c) and 5 to 40 mol % of diamino radicals (d), based on said diamine radicals.

11. A process according to claim 10, wherein the copolyamide or copolyimide-amide contains 75 to 95 mol % of diamine radicals (c) and 5 to 25 mol % of diamino radicals (d).

12. A process according to claim 1, wherein the copolyimide or copolyimide-amide or a copolymer thereof has an inherent viscosity of 0.2 to 3.0 dl/g, measured at 5° C. in a solution of 0.5% by weight of said copolymers in N-methylpyrrolidone.

13. A process according to claim 1, wherein M is $H^\oplus$, $NH_4^\oplus$, an alkali metal cation or a primary, secondary, tertiary or quaternary ammonium cation of 1 to 24 carbon atoms.

14. A process according to claim 1, wherein the copolyamide and/or copolyimide-amide comprises a) 60 to 95 mol % of at least one structural repeating unit of formulae I and/or Ia,

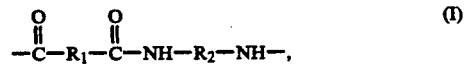
(I)

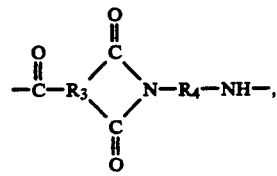
(Ia)

and b) 5 to 40 mol % of at least one structural repeating unit of formulae II and/or IIa,

(II)

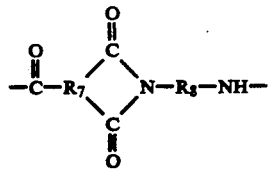
(IIa)

based on the copolymers, wherein wherein $R_1$ and $R_5$ are each independently of the other a radical of formula

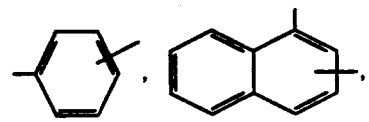

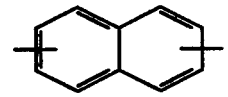

-continued
or

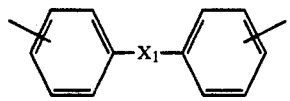

which radical is unsubstituted or substituted by Cl, Br, NO$_2$, C$_1$-C$_4$alkyl or C$_1$-C$_4$alkoxy, in which formulae X$_1$ is a direct bond, CH$_2$, $-(CH_2)_2-$, $-HC=CH-$,

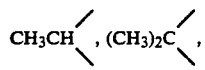

$-NR_9-$, $-N=N-$, $-CO-$, $-O-$, $-S-$, $-SO-$ or $-SO_2-$, and R$_9$ is H or C$_1$-C$_6$alkyl, R$_3$ and R$_7$ are each independently of the other a radical of formulae

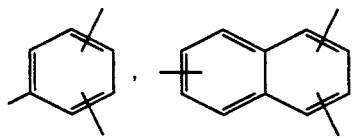

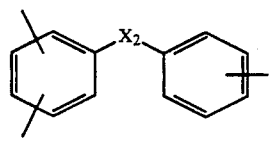

wherein two bonds are linked to two adjacent carbon atoms, and X$_2$ independently has the same meaning as X$_1$, R$_2$ and R$_4$ are each independently of the other an unsubstituted or chloro-, bromo- or C$_1$-C$_4$alkyl-substituted radical of formulae

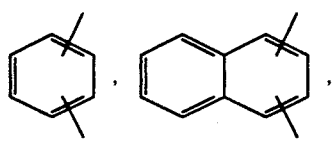

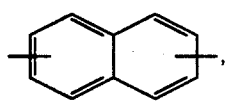

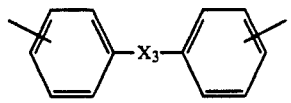

wherein X$_3$ independently has the same meaning as X$_1$, and

R$_6$ and R$_8$ are each independently of the other a radical of formulae

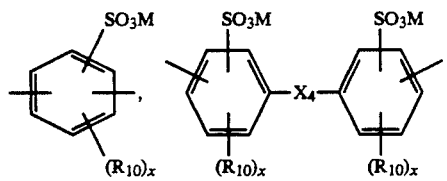

wherein X$_4$ independently has the same meaning as X$_1$, R$_{10}$ is C$_1$-C$_4$alkyl, x is 0, 1, 2 or 3 and M is H$^\oplus$, NH$_4^\oplus$, an alkali metal cation or a primary, secondary, tertiary or quaternary ammonium cation of 1 to 24 carbon atoms.

15. A process according to claim 14, wherein the copolyamide comprises structural units of formulae I and II, and X$_1$ and X$_4$ are each independently of the other a direct bond, $-CH_2-$, $-CO-$, $-O-$ or $-S-$.

16. A process according to claim 14, wherein the structural units of formula II of the copolyamide R$_1$ and R$_5$ are each independently of the other m-and/or p-phenylene which are unsubstituted or substituted by $-NO_2-$, $-Cl$ or $-Br$, R$_2$ is unsubstituted phenylene or phenylene which is substituted by $-Cl$, $-Br$, methyl or ethyl, or is 3,3'- or 4,4'-diphenylmethanediyl which is substituted in both o-positions to the amino groups by methyl and/or ethyl, and R$_6$ is a radical of formulae

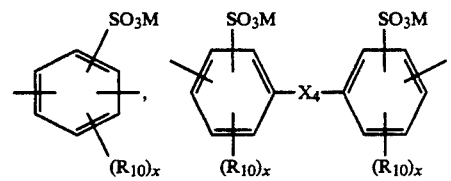

wherein X$_4$ is a direct bond or $-CH_2-$, R$_{10}$ is methyl or ethyl, x is 1, 2 or 3, and M is H$^\oplus$, NH$_4^\oplus$, Li$^\oplus$, Na$^\oplus$, K$^\oplus$, Rb$^\oplus$, Cs$^\oplus$ or quaternary ammonium of 4 to 16 carbon atoms.

17. A process according to claim 16, wherein R$_6$ is a radical of formula

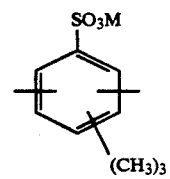

wherein M is H$^\oplus$, NH$_4^\oplus$, Li$^\oplus$, Na$^\oplus$, K$^\oplus$, Rb$^\oplus$, Cs$^\oplus$ or quaternary ammonium of 4 to 16 carbon atoms.

* * * * *